US008734430B2

(12) United States Patent
Holmes

(10) Patent No.: US 8,734,430 B2
(45) Date of Patent: May 27, 2014

(54) SUSTAINED RELEASE CAPSULES

(75) Inventor: Robert William Lachlan Holmes, North Shore (NZ)

(73) Assignee: Merial Limited, Duluth, GA (US)

( * ) Notice: Subject to any disclaimer, the term of this patent is extended or adjusted under 35 U.S.C. 154(b) by 50 days.

(21) Appl. No.: 13/386,202

(22) PCT Filed: Jul. 16, 2010

(86) PCT No.: PCT/NZ2010/000146
§ 371 (c)(1),
(2), (4) Date: Jan. 20, 2012

(87) PCT Pub. No.: WO2011/014078
PCT Pub. Date: Feb. 3, 2011

(65) Prior Publication Data
US 2012/0123394 A1 May 17, 2012

(30) Foreign Application Priority Data

Jul. 31, 2009 (NZ) .................................. 578771

(51) Int. Cl.
| A61K 9/22 | (2006.01) |
| A61M 31/00 | (2006.01) |
| A61M 5/20 | (2006.01) |
| A23K 1/18 | (2006.01) |
| A61F 13/00 | (2006.01) |

(52) U.S. Cl.
USPC .......... 604/891.1; 604/57; 604/135; 424/438; 424/422

(58) Field of Classification Search
CPC .......... A61M 5/14276; A61M 31/002; A61M 2205/3523; A61M 39/0208; A61M 1/0039; A61M 3/0279; A61M 1/0056; A61M 31/00; A61M 37/0069; A61M 5/2033; A61M 2005/206; A61M 5/1454; A61M 5/24; A61M 2005/14506; A61K 9/0024; A61K 9/0036; A61K 9/0068; A61K 9/0004; A61B 17/3468; A61D 7/00; A23K 1/1813; A23K 1/005; A23K 9/0004; A23K 9/0024; A61L 31/10; A61L 31/16; A61L 27/54; A61L 27/34

USPC ................. 604/890.1, 891.1, 892.1, 57, 48, 604/131–133, 135, 140–143, 150; 424/438, 424/422

See application file for complete search history.

(56) References Cited

U.S. PATENT DOCUMENTS

| 4,416,659 A | * 11/1983 | Simpson et al. ................. 604/48 |
| 4,671,789 A | 6/1987 | Laby |
| 2003/0212386 A1 | 11/2003 | Trompen |
| 2005/0064032 A1 | 3/2005 | Lowe et al. |

FOREIGN PATENT DOCUMENTS

| AU | 2005209631 A1 | 3/2006 |
| EP | 0174865 A2 | 3/1986 |
| EP | 0507629 B1 | 1/1997 |
| EP | 0627231 B1 | 4/2002 |
| WO | WO 9535131 A1 | 12/1995 |
| WO | WO 2005046639 A2 | 5/2005 |

* cited by examiner

Primary Examiner — Bhisma Mehta
Assistant Examiner — Niyati D Shah
(74) Attorney, Agent, or Firm — Judy Jarecki-Black; Chad Kitchen; Merial Limited

(57) ABSTRACT

The invention relates to an intraruminal sustained release capsule which is capable of delivering a sustained release dose of a first medicament to an animal, as well as either or both of a dump dose of a second medicament or mineral, and an exit dose of a third medicament or mineral. The capsule can have a dissolvable overcap molded from plasticized starch enabling a dump dose of medicament to be held between the overcap and one end of the capsule. A piston within the body of the capsule can be modified to enable it to accommodate an exit dose of medicament within its hollow interior which is aligned with an aperture at the end of the capsule which enables release of the medicaments to the rumen. After insertion of the capsule in the animal the overcap (if present) dissolves and separates from the capsule to release the dump dose of medicament. The sustained release medicament is then dispensed via the apertured end, followed by the release of the exit dose of medicament (if present).

11 Claims, 7 Drawing Sheets

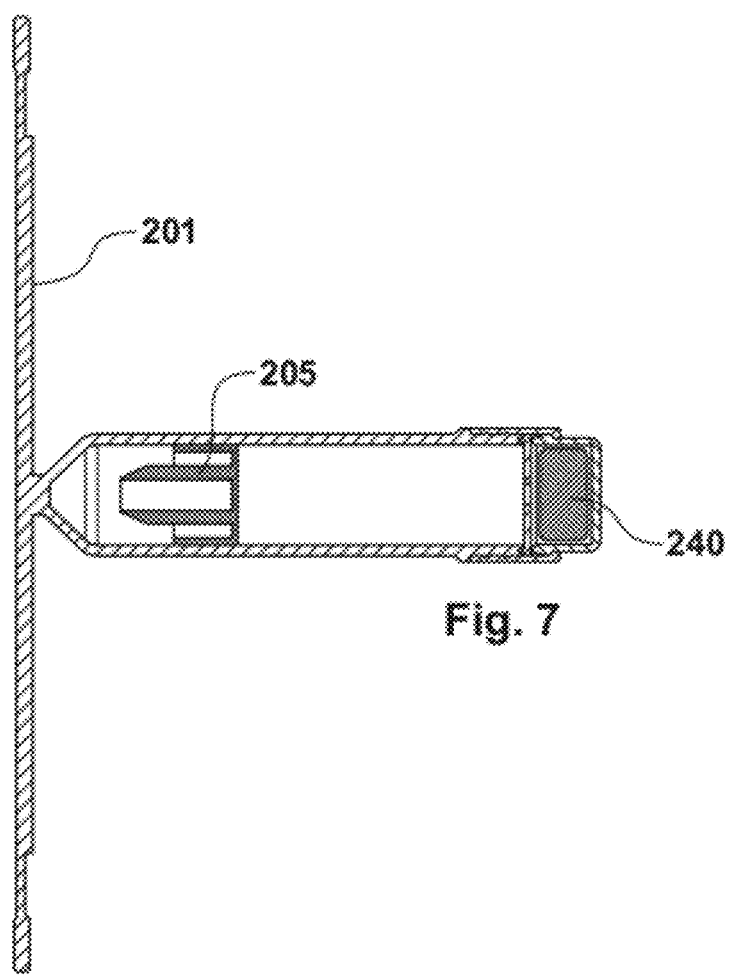

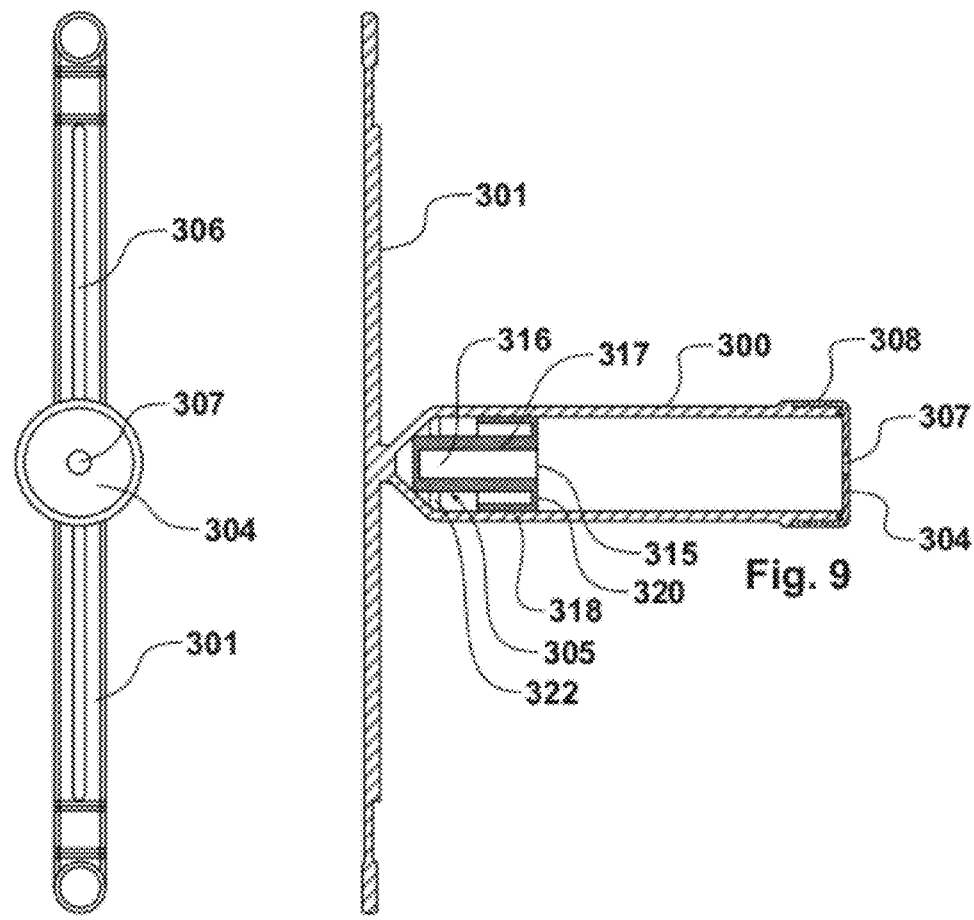
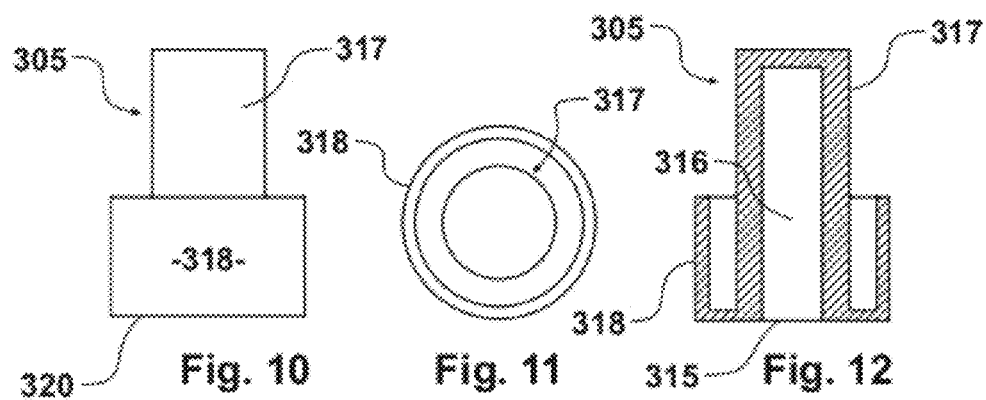

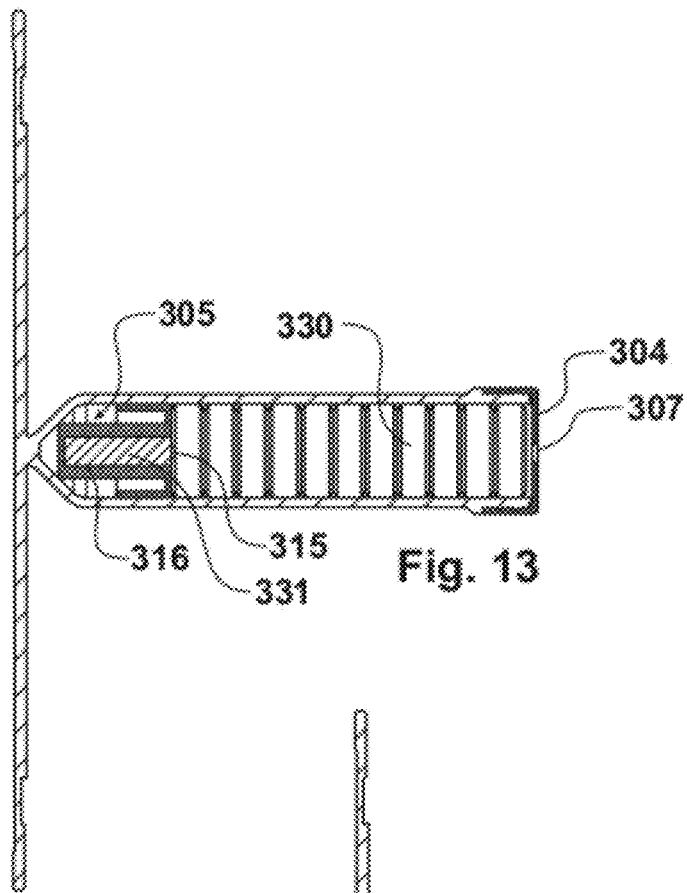
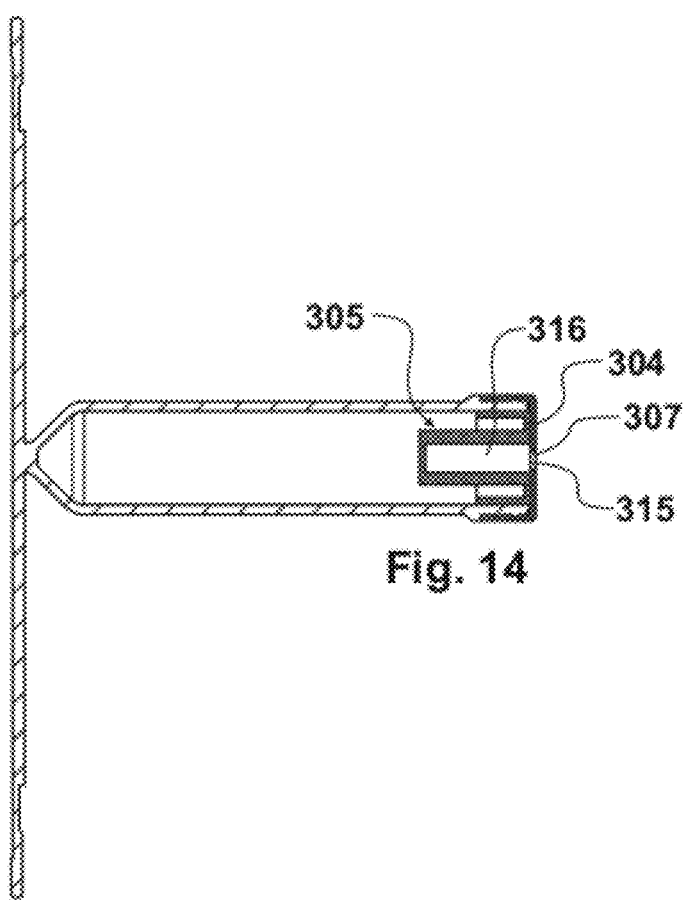

SUSTAINED RELEASE CAPSULES

FIELD OF THE INVENTION

This invention relates to an intraruminal device, and more particularly to an intraruminal sustained release capsule designed to release two or more active ingredients into the rumen of a ruminant animal, such as a sheep, cow, goat, deer etc.

BACKGROUND OF THE INVENTION

There are a number of intraruminal devices and sustained release capsules and formulations presently available. In general the devices currently available are in the form of a capsule, which comprises: a substantially hollow tubular body, which is sealed at one end by a cap, and partially sealed at the second end by an annular flange, which defines an opening. There is provision within the body for the inclusion of a solid therapeutic composition.

Many of the currently available intraruminal devices contain a spring and plunger mechanism for urging the solid therapeutic composition towards the opening. The cap end may also have attached to it a plurality of resilient arms designed to prevent regurgitation of the device by the animal.

Intraruminal devices are inserted through the oesophagus into the animal's rumen. Once in the rumen they commence the release of the therapeutic composition over a prolonged period of time. A number of such formulations are available which are all capable of releasing a single therapeutic drug, such as an anthelmintic, and in some cases a range of supplementary trace elements.

Sustained release capsules have been available for over fifteen years. These devices release active ingredients or trace elements into the rumen of an animal for a period of 90-180 days.

There are two main types of sustained released capsule:
Simple Erodible Systems

These were the first type of sustained release device introduced to the market. They are generally of a waxy or metallic construction and are in the shape of a simple cylinder. Erosion either occurs from over the entire surface of the device, or in some cases the device may have been dipped in a coating material so that only the ends of the device are exposed. In this case payout will be able to be controlled more effectively. The interaction with the rumen contents (amount of grass and liquid content) determines the rate of erosion of the device.

Examples of such devices include:
Alltrace Mineral Bolus (Agrimin, UK)—This is an erodible bolus containing: Copper (16,379 mg), Cobalt (236 mg), Selenium (251 mg), Manganese (8,326 mg), Zinc (13,382 mg), Iodine (497 mg), Vitamin A (549,408 i.u.), Vitamin D (3109,881 i.u.) and Vitamin E (1,099 i.u.). Two boluses are administered to each animal weighing 150 kgs or more, with the payout period being 240 days. To retain the bolus in the rumen the device has a sold metal densifier element which erodes after the lighter mineral elements have dissolved. The advantage of the device is the high loading of active ingredients and the fact that the device will fully erode leaving no part retained in the animal. Disadvantage of this style of erodible bolus is that it is not possible to achieve a linear release rate.

Optimag Magnesium Bolus (Norbrook, UK)—A solid metallic bolus containing 100 g of magnesium released over approximately 4 weeks. These are used in adult cattle as an aid to maintenance of magnesium intake.

In both of the above cases the aim of bolus administration is to maintain mineral levels in the treated animal for a prolonged period of time. Neither device allows for complex payout profiles as might be required if the farmer wished to deliver an immediate short-acting dose of a particular active ingredient to be followed by the sustained payout of the minerals in question.

Sustained-Release Devices

A relatively new technology is the category of sustained-release devices. In general these are in the form of a plastic capsule, comprising: a substantially hollow tubular body, which is completely sealed at one end by a cap, and partially sealed at the second end by an annular flange, which defines an opening. There is provision within the body for the inclusion of a solid therapeutic composition.

Many of the currently available sustained release devices contain a spring and plunger mechanism for urging the solid therapeutic composition (either in the form of solid wax or stack of tablets) towards the opening. Other devices rely on osmotic pressure to expand a driver portion in the base of the capsule. This driver portion causes the active contents to be expelled from the open end of the capsule. The diameter of the opening can be used to increase or restrict the speed of payout of the device.

The capsule may be retained in the rumen of the animal either by a plurality of resilient arms protruding from the cap end of the device, or by a weighted metal densifier element within the body of the device.

Typically this style of device is used to deliver active ingredients requiring a greater precision of payout such as anthelmintics. In these cases the daily dose of anthelmintic is low compared to the amount recommended in a standard oral dose.

Examples of sustained release devices include:
IVOMEC SR Bolus (MSD Agvet)—Containing 1.72 g ivermectin releasing over 140 days. This device uses osmotic pressure to expand a driver portion in the base of the capsule. The expansion of this driver portion urges the solid wax formulation containing ivermectin towards the opening.
EXTENDER SeCo (Merial)—Containing 4.62 g albendazole releasing over 100 days, and IVOMEC Maximizer Capsule (Merial)—Containing 160 mg ivermectin releasing over 100 days. Both of these devices utilise a spring portion to urge a stack of tablets containing the active ingredients towards the opening. At the opening the face of the exposed tablet forms a gel which is released into the rumen.

There are times however when even sustained release of one or more substances over a prolonged period is insufficient to satisfy animal health needs. In certain cases the farmer may wish to deliver an additional substance in an immediate or dump release fashion prior to or following the period of sustained release.

Examples of such cases could include:
When a secondary trace element or mineral treatment is required to be given to an animal at the same time as a sustained release treatment of an anthelmintic. Traditionally this would mean that the farmer would administer a separate treatment in the form of a liquid drench or oral capsule. An example of this is that farmers will often give a copper oxide needle treatment in the form of a gelatine capsule for preventing copper deficiency. It can be recognised that this separate treatment is time consuming and inconvenient.

A further example is that the manufacturers of EXTENDER SeCo recommend that a large "primer" or initial dose of an effective oral anthelmintic is given at the same time as the capsule is inserted into the animal. The purpose of this primer dose is to control the adult stage parasites that are resident in the animal. Once this is done the capsule will be able to effectively control any new incoming larvae for the effective payout period of the device.

Another example is that there is a concern that some single active sustained release anthelmintic devices may not effectively control all parasites for the full duration of the payout period. In some cases it may be desirable to administer to the animal what is known as an "exit" dose. This is a large dose of anthelmintic administered at a single time point sufficient to control adult parasites that may have survived the smaller sustained dose of anthelmintic.

Recently there have been attempts to incorporate priming and/or exit doses into sustained release capsules so that there is no need for the farmer to administer a separate treatment.

These are typically made by incorporating one or more fast releasing tablets into the stack of sustained release tablets contained within the device. These fast release tablets contain disintegrants and effervescent materials. Unfortunately the fast release of the tablet can allow moisture to seep through the annular flange defining the opening and down the inside of the capsule body. This can then impede release of subsequent sustained release tablets.

OBJECT OF THE INVENTION

It is an object of the present invention to provide an improved intraruminal device and/or an improved sustained release capsule or one which will at least provide the public with a useful choice.

STATEMENT OF INVENTION

In a first aspect the invention provides a sustained release capsule comprising a hollow tubular body sealed at a first end, a movable piston within the body, a spring biasing the piston towards a second end of the body, an apertured cover at the second end to define a first chamber between the movable piston and the apertured cover capable of containing a first dose of material within the hollow tubular body for subsequent sustained release through the apertured cover into the rumen of an animal, wherein an overcap is releasably attached to the device at one end thereof to form a void between an end of the device and the overcap capable of containing a second dose of material within the void so that in use the second dose of material is delivered to the rumen when the overcap is breached or detaches from the device.

Preferably the overcap is attached to the second end of the device to form a void between the apertured cover and the overcap capable of containing the second dose of material within the void so that in use the second dose of material is delivered to the rumen when the overcap is breached or detaches from the second end.

Preferably the overcap is releasably attached to the capsule by a dissolvable attachment.

Preferably the overcap is made of a material which will dissolve or breakup in the rumen.

Preferably the overcap is made of a material selected from the group comprising cellulosic fibre, cardboard, paper, a water soluble plastics material, and starch.

Preferably the body has at least one external protrusion adapted in use to assist in retaining the capsule in the rumen of an animal.

Preferably the at least one protrusion consists of a pair of foldable wings.

Preferably the capsule is loaded with a first dose of material.

Preferably the capsule is loaded with a second dose of material in the overcap.

Preferably the second dose of material in the overcap comprises copper needles.

Alternatively this material in the overcap may comprise one or more anthelmintics.

In a second aspect the invention provides a sustained release capsule comprising a hollow tubular body sealed at a first end, a movable piston within the body, a spring biasing the piston towards a second end of the body, an apertured cover at the second end to define a first chamber between the movable piston and the apertured cover capable of containing a first dose of material within the hollow tubular body for subsequent sustained release through the apertured cover into the rumen of an animal, wherein an overcap is releasably attached to the second end to form a void between the apertured cover and the overcap capable of containing a second dose of material within the void so that in use the second dose of material is delivered to the rumen when the overcap is breached or detaches from the second end.

Preferably the overcap is releasably attached to the second end by a dissolvable attachment.

Preferably the overcap is made of a material which will dissolve or breakup in the rumen.

Preferably the overcap is made of a material selected from the group comprising cellulosic fibre, cardboard, paper, a water soluble plastics material, and starch.

Preferably the body has at least one external protrusion adapted in use to assist in retaining the capsule in the rumen of an animal.

Preferably the at least one protrusion consists of a pair of foldable wings.

Preferably the capsule is loaded with a first dose of material.

Preferably the capsule is loaded with a second dose of material in the overcap.

Preferably the second dose of material in the overcap comprises copper needles.

Alternatively this material in the overcap may comprise one or more anthelmintics.

In a third aspect the invention provides a sustained release capsule comprising a hollow tubular body sealed at a first end, a movable piston within the body, a spring biasing the piston towards a second end of the body, an apertured cover at the second end to define a first chamber between the movable piston and the apertured cover capable of containing a first dose of material within the hollow tubular body for subsequent sustained release through the apertured cover into the rumen of an animal, wherein the movable piston has an end face facing towards the first dose, a hollow central sleeve extending rearwardly from the end face to assist in locating a spring, an aperture in the end face into the hollow interior of the central sleeve, the central sleeve having a closed portion distal from the end face to create a void capable of containing an exit dose of material.

Preferably the piston further includes an optional outer sleeve separated from the central sleeve to create an annular void capable of containing the spring.

Preferably the sustained release capsule further includes an overcap which is releasably attached to the second end to form a void between the apertured cover and the overcap capable of containing a second dose of material within the void so that in use the second dose of material is delivered to the rumen when the overcap is breached or detaches from the second end.

Preferably the overcap is releasably attached to the second end of the capsule by a dissolvable attachment.

Preferably the overcap is made of a material which will dissolve or breakup in the rumen.

Preferably the overcap is made of a material selected from the group comprising cellulosic fibre, cardboard, paper, a water soluble plastics material and starch.

Preferably the body has at least one external protrusion adapted in use to assist in retaining the capsule in the rumen of an animal.

Preferably at least one protrusion consists of a pair of foldable wings.

Preferably the capsule is loaded with a first dose of material.

Preferably the capsule is loaded with a second dose of material in the overcap.

Preferably the capsule is loaded with an exit dose of material.

Preferably the second dose of material in the overcap comprises copper needles.

Alternatively this material in the overcap may comprise one or more anthelmintics.

Preferably the sustained release capsule contains a dump dose of material within the overcap, a sustained release dose of material within the body of the capsule and an exit dose of material within the piston.

In a fourth aspect the invention provides a sustained release capsule comprising a hollow tubular body sealed at a first end, a movable piston within the body, a spring biasing the piston towards a second end of the body, an apertured cover at the second end to define a first chamber between the movable piston and the apertured cover capable of containing a first dose of material within the hollow tubular body for subsequent sustained release through the apertured cover into the rumen of an animal, wherein the movable piston has an end face facing towards the first dose, a hollow central sleeve extending rearwardly from the end face to assist in locating a spring, an aperture in the end face into the hollow interior of the central sleeve, the central sleeve having a closed portion distal from the end face to create a void capable of containing an exit dose of material, and wherein an overcap is releasably attached to the device at one end thereof to form a void between an end of the device and the overcap capable of containing a second dose of material within the void so that in use the second dose of material is delivered to the rumen when the overcap is breached or detaches from the device.

Preferably the piston further includes an optional outer sleeve separated from the central sleeve to create an annular void capable of containing the spring.

Preferably the overcap is attached to the second end of the device to form a void between the apertured cover and the overcap capable of containing the second dose of material within the void so that in use the second dose of material is delivered to the rumen when the overcap is breached or detaches from the second end.

Preferably the overcap is releasably attached to the capsule by a dissolvable attachment.

Preferably the overcap is made of a material which will dissolve or breakup in the rumen.

Preferably the overcap is made of a material selected from the group comprising cellulosic fibre, cardboard, paper, a water soluble plastics material, and starch.

Preferably the body has at least one external protrusion adapted in use to assist in retaining the capsule in the rumen of an animal.

Preferably the at least one protrusion consists of a pair of foldable wings.

Preferably the capsule is loaded with a first dose of material.

Preferably the capsule is loaded with a second dose of material in the overcap.

Preferably the capsule is loaded with an exit dose of material.

Preferably the second dose of material in the overcap comprises copper needles.

Alternatively this material in the overcap may comprise one or more anthelmintics.

Preferably the sustained release capsule contains a dump dose of material within the overcap, a sustained release dose of material within the body of the capsule and an exit dose of material within the piston.

DRAWINGS

These and other aspects of this invention, which should be considered in all its novel aspects, will become apparent from the following description, which is given by way of example only, with reference to the accompanying drawings, in which:

FIG. 1 is a side elevation of a first embodiment of the invention capable of providing a dump dose of material.

FIG. 2 is a cross-sectional view on lines A-A through the capsule body of FIG. 1.

FIG. 3 is an enlarged sectional view of the overcap of FIG. 1.

FIG. 4 shows a side elevation of a second embodiment of the invention capable of providing a dump dose of material.

FIG. 5 is a cross-sectional view on lines A-A through the capsule body of FIG. 4.

FIG. 6A is an enlarged sectional view of the overcap of FIG. 4.

FIG. 6B is a further enlarged sectional view of part of the overcap of FIG. 6A.

FIG. 7 shows a side elevation of the second embodiment of the invention showing a dump dose tablet contained within the overcap.

FIG. 8 is an end elevation of a third embodiment of the invention capable of providing an exit dose of material.

FIG. 9 shows a cross-sectional view of the exit dose embodiment of FIG. 8.

FIG. 10 shows an enlarged side elevation of a piston for insertion in the capsule.

FIG. 11 is an end elevation of the piston of FIG. 10.

FIG. 12 shows a cross-sectional view of the piston of FIG. 10.

FIG. 13 shows a similar cross-sectional view to that of FIG. 9 but this time fully loaded with tablets between the piston and the apertured cover (before dispensing commences) and an exit dose loaded within the cavity of the central sleeve of the piston.

FIG. 14 shows a cross-sectional view of the capsule of FIG. 13 after the sustained released tablets have been dispensed and the piston is fully extended so that the exit dose can be dispensed via the aperture in the cover.

FIG. 15 shows a cross sectional view of a capsule described in example 4 with the wings folded. This capsule combines both the dump dose and the exit dose arrangements.

FIG. 16 is a cross sectional view of the capsule of FIG. 15 but with the wings extended.

DESCRIPTION OF DRAWINGS

The following description will describe the invention in relation to preferred embodiments of the invention, namely a sustained release capsule.

The invention is in no way limited to these preferred embodiments as they are purely to exemplify the invention only and it should be understood that possible variations and modifications which would be readily apparent are intended to be included without departing from the scope of the invention.

There are two aspects to the current invention. The first aspect addresses the need to provide a priming dose capability for a sustained release capsule, while the second aspect addresses the need to provide the exit dose capability.

Priming Dose

The first preferred embodiments of this invention are designed to achieve an outcome whereby a secondary treatment formulation can be mounted with the sustained release device without requiring modifications to the geometry of the device that would impede subsequent payout from the sustained release portion. This is achieved by holding the secondary treatment, which could be in the form of a liquid, powder, fine particles or tablets under a releasable or detachable overcap mounted on one end of the device. This overcap is able to be constructed of moulded fibre, cardboard or preferably a biodegradable starch material and would serve the purpose of protecting the secondary treatment during storage and transport.

Because the overcap would rapidly detach from the capsule once it was in the rumen it would leave the basic geometry of the sustained release capsule unchanged. Preferably the release of the overcap results from the rumen fluid causing the material of the cap to dissolve and/or biodegrade. However, in other embodiments of the invention the overcap can be made of a material that is more durable and is attached to the capsule by a soluble tape or the like, such that the release of the overcap results from the rumen fluid causing the soluble tape to dissolve and/or biodegrade. In this case the more durable material is likely to be made of a material which will eventually biodegrade inside the animal even if it biodegrades at a slower rate than the soluble tape.

Example 1

Figure 1:
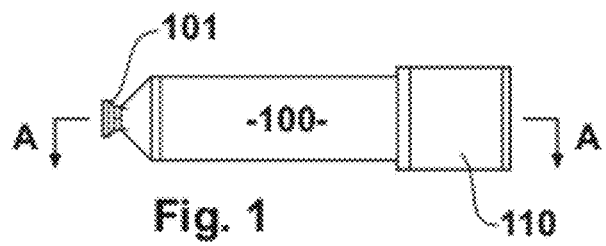
Figure 2:
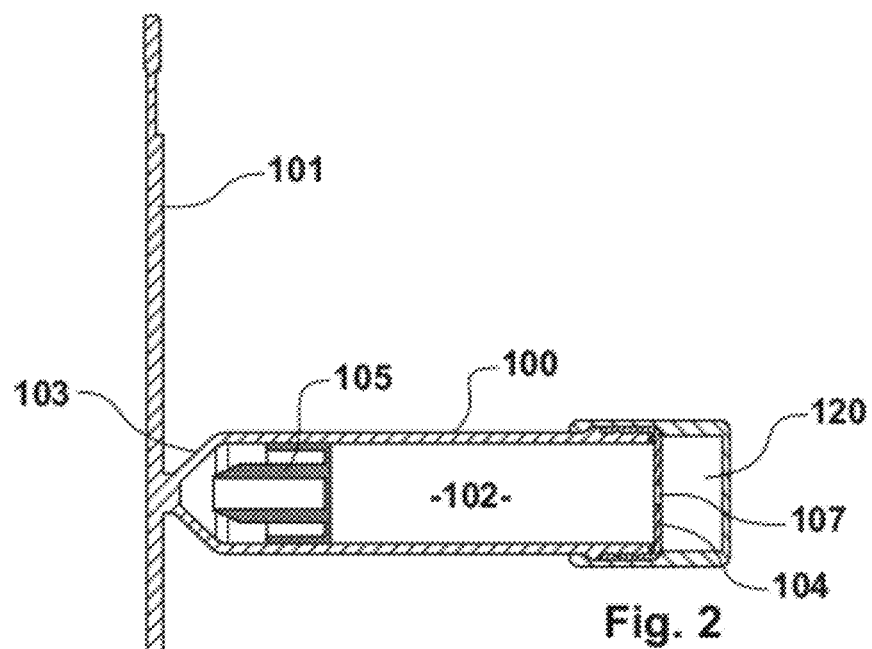
Figure 3:
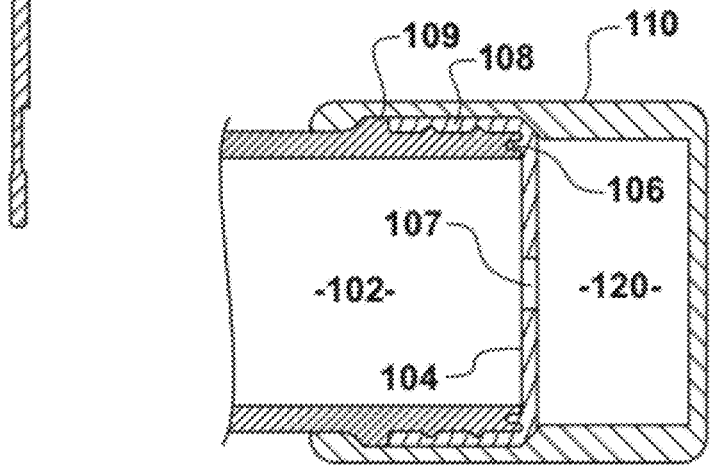

FIGS. 1-3 of the attached drawings provide an example of a first embodiment of the invention, which is capable of providing a dump dose of material to the rumen of a ruminant animal. In this embodiment of the invention, an overcap, preferably made of a starch material is mounted on the end of the main capsule device.

The capsule 100 is shown in side elevation in FIG. 1. The capsule 100 has foldable wings 101 which when extended protrude at right angles to the page. The extended wings are shown in cross sectional view in FIG. 2, cross section being taken on lines AA of FIG. 1. The capsule 100 has an overcap 110 mounted on one end.

The capsule 100 and foldable wings 101 may be of a generally conventional construction having a moveable piston inside the body of the capsule 100, and as shown in FIG. 2 this is at or adjacent the closed end 103, the moveable piston 105 having a closed end face which pushes against a stack of tablets or other medicament (not shown) contained in the void 102 within the capsule 100. The other end of the capsule 100 has a closed end 104 having a central aperture 107. This is shown in more detail in the enlarged view of the overcap shown in FIG. 3. In this view, the closed end 104 is shown attached to the body of the capsule by means of a screw thread or clip on attachment 108, which also has a sealing rib 109 beyond the end of the screw thread 108. There is also a sealing lip 106 which mates with a groove in the end of the capsule body, to prevent leakage of rumen fluid into the body of the capsule other than via aperture 107, and conversely prevent the leakage of medicament around the edge of the end face 104.

With the exception of the overcap 110 and its attachment to the capsule 100, the other components of the capsule device 100, 101, 102, 103, 104, and 105 can be of conventional sustained release capsule construction.

In this embodiment of the invention the novel feature is the provision of an overcap 110, which is preferably made of a mouldable starch material, and which is of a sufficient shape and size so as to fit snugly over the end face 104 of the capsule, and clip over the sealing rib 109. Thus the diameter of the overcap 110 is only slightly greater than the diameter of the capsule body 100. The overcap 110 preferably has a rounded nose and rounded end, so as not to provide any obstruction or discomfort when the device is swallowed by the animal being treated.

The moulded overcap 110 is of such a size and shape so as to provide a void 120 between the closed end 104 of the capsule and the inside edges of the overcap, the void being for the inclusion of a dump dose of a medicament. The medicament might be in the form of a specially formulated tablet which is designed for rapid release in the rumen once the overcap has been dissolved or detached or otherwise breached by the rumen fluid, or it might be a collection of copper oxide needles or particles, or any other dose which is to be administered to the animal prior to the release of the sustained release pay load contained within the void 102 in the body of the capsule. In some cases the dump dose medicament might be a fast acting anthelmintic, to flush out any adult parasites, whilst the medicament in the sustained release portion of the device consists of a long acting anthelmintic designed to treat the immature and juvenile parasites. Of course many other combinations are possible.

Prior to administration of the capsule, the wings 101 will be folded down and attached to the sides of the capsule 100. As shown in FIG. 2 the wings 101 may be of a length such that they extend slightly over the overcap, and thus the ends of the wings 101 may be narrowed or tapered in order to fit snugly against the end of the overcap when they are folded down. The wings 101 can be then secured to the body of the capsule or the overcap by suitable quick release means, typically a water soluble or dissolvable tape, which will degrade quickly once the capsule has been inserted into the rumen, thereby releasing the wings so they extend into the protruding position as shown in FIG. 2 in order to prevent regurgitation of the capsule by the animal being treated.

By modifying the properties of the starch the overcap 110 can be dissolved by the rumen fluid, and depending upon the size and thickness of the overcap, the overcap will then start to jellify, and detach from the body of the capsule 100. In the most preferred form of the invention, the overcap 110 is designed to detach from the body of the capsule, as the wall thickness of the overcap is thinner adjacent the screw threaded portion 108 of the end portion of the capsule. However it is possible that the overcap could be designed to be breached in other portions or areas before actually detaching, so that the dump dose of medicament can be quickly released into the rumen even if the overcap has not itself been detached from the capsule body.

Once the dump dose of medicament has been released either by the cap detaching, or the cap being breached, rumen fluid can then enter the aperture 107 of the capsule body, and the sustained release payload contained in the void 102 will start being dispensed as it is dissolved by the rumen fluid. During this time the moveable piston 105 is biased towards the stack of tablets or capsules or other medicament contained within the void 102, and as the medicament dissolves the piston moves towards the closed end 104 of the capsule.

Example 2

FIGS. 4-7 of the attached drawings provide an example of a second embodiment of the invention, which is capable of providing a dump dose of material to the rumen of a ruminant animal. In this embodiment of the invention, an overcap, preferably made of a starch material is retained on the inside of a lip on the end of the main capsule device.

Figure 4:
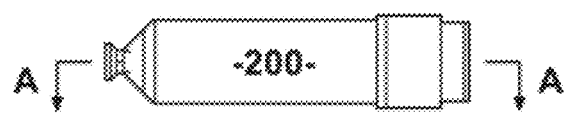
Figure 5:
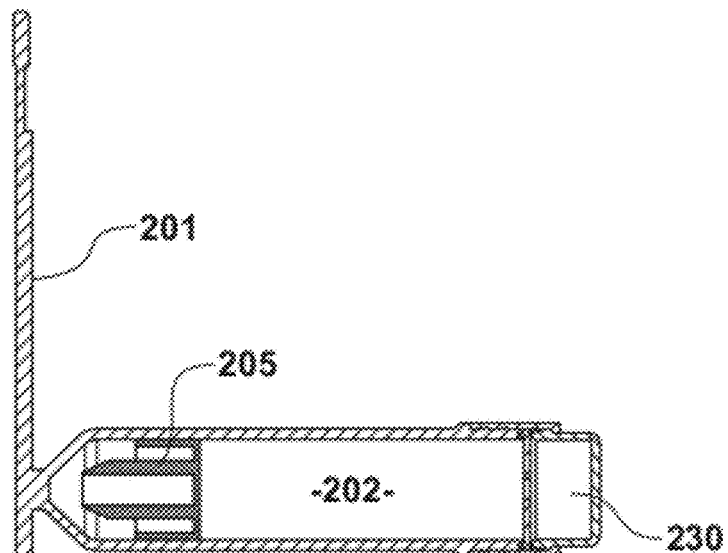
Figure 6A:
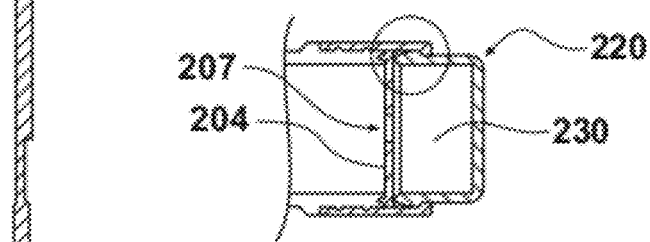
Figure 6B:
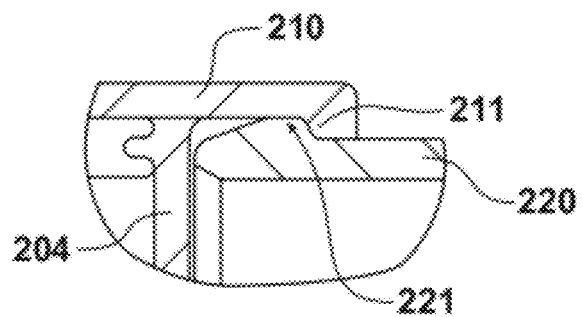

The capsule 200 is shown in side elevation in FIG. 4. Again, the capsule 200 has foldable wings 201 which extend as shown in the cross sectional view in FIG. 5, cross section being taken on lines A-A of FIG. 4. The capsule 200, having void space 202, has an overcap 230 mounted on one end. The capsule has wings 201 and a moveable piston 205 in a similar arrangement to that of the first embodiment described in example 1. The difference between these two embodiments of the invention is shown in more detail in FIGS. 6A and 6B. The closed end 204 of the capsule having the central aperture 207 now extends rearwardly to form a rearwardly extending sleeve 210 having an inwardly facing circumferential lip 211. The overcap 220 has an outwardly facing circumferential protrusion 221 designed to fit under the lip 211, in order to attach the overcap to the capsule. The overcap 220 is preferably made of a hollow moulded starch material, thereby defining a void 230. The void 230 is designed to contain a dump dose of a medicament. FIG. 7 shows a side view of the capsule which contains a dump dose of a medicament within the overcap in the form of a single tablet 240. The medicament could however be in any desired form.

It is noted that in Examples 1 and 2 the overcap prevents any rumen fluid from entering the aperture 107 or 207 until the overcap has been detached from the end of the capsule device, or until the overcap has been breached and the dump dose of medicament has been released.

Preferred Materials

In the preferred embodiments of the invention, the overcap is made entirely of an acceptable dissolvable material such as potato or corn starch (e.g. Plastarch) or alternatively Polylactide acid (e.g. Cereplast Compostables material). Pure starch possesses the characteristic of being able to absorb moisture and is thus ideally suited for this application. Flexibilisers and/or plasticisers such as sorbitol and glycerine may be added to the starch so that the starch can be injection molded into the desired shape.

Upon contact with the rumen fluids the overcap will begin to gellify and become detached from the capsule. Once the overcap is detached, the dump dose of medicament located within or underneath the overcap is released into the rumen.

The capsule 100 or 200 and wings 101 or 201 and end closure 104 or 204 can all be moulded of a suitable plastics material.

Advantages of the Dump Dose Configurations

The use of the plasticised starch material for the overcap has a secondary and unexpected benefit in that it develops a slippery surface on contact with saliva/mouth moisture, which can aid passage of the capsule down the oesophagus of the animal when treated.

The thickness of the walls of the overcap can be adjusted in order to alter the time taken to separate the overcap from the capsule device.

The fact that the overcap can become entirely separated from the capsule means that there is no interaction or interference with the dynamics of release of the sustained release medicament from the body of the capsule.

Variations of the Dump Dose Configurations Include:

Anthelmintic release devices—a primary dose of one or more active ingredients is formulated in one or more tablets. This dose is stored under the overcap. The overcap is mounted at the opening end of the capsule. Within the capsule body is a plurality of tablets or a stack of tablets containing a sustained release formulation of one or more anthelmintics.

Mineralised capsules—in which a primary dose of copper oxide wire particles is stored under the overcap. Once again the overcap is mounted at the opening end of the capsule. Within the capsule body is a plurality of tablets or a stack of tablets containing a sustained release formulation of one or more minerals such as selenium and cobalt.

It should be recognised that there are many combinations and permutations of medicaments that are capable of being used with this invention. For example the overcap may contain any number of individual materials each having a different biological effect.

It is also possible that the overcap could be constructed of other types of material such as cardboard or plastic. The overcap could be attached to the capsule by means of a clip or alternatively by water soluble adhesive tape or some other non-permanent attaching means.

One such variation could be the use of an overcap made of cardboard or plastic which is secured to the end of the capsule body by means of the same dissolvable tape used to hold the wings in place. In another version the wings may well have a provision which clips into the cardboard or plastic overcap, and the wings are then held in place by a dissolvable tape so that once the tape has been released, the movement of the wings will cause the plastic or cardboard overcap to be detached from the dump dose body.

Although the preferred embodiments have been described with reference to the overcap fitting over the closed end of the capsule, i.e. at the end distant from the attachment of the wings, it will be appreciated that the overcap could be positioned at the same end of the capsule where the wings are attached.

Figure 15:
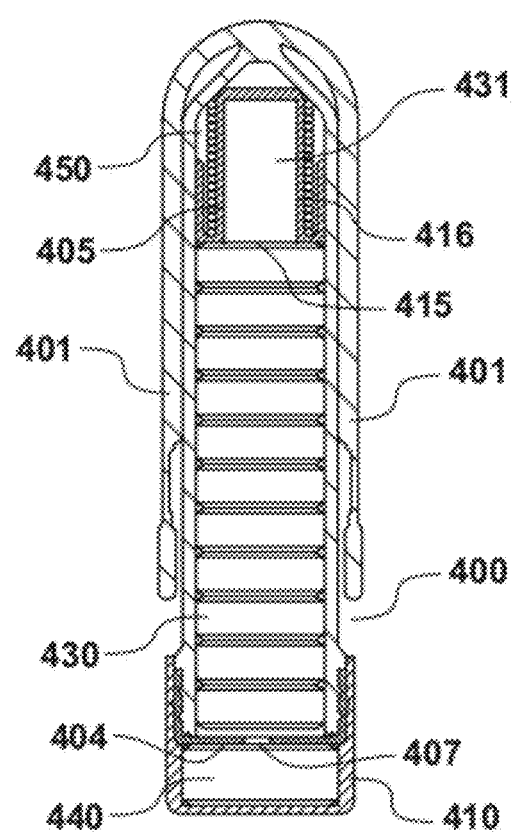

In such an arrangement, the wings will be folded down prior to administration of the capsule to the animal, in the position shown in FIG. 15, and taped in place. The overcap can then be fitted over the end of the capsule adjacent the hinge point of the wings, so that the overcap would sit over the folded wings. Taping of the overcap to the capsule enfolded wings could also serve to hold the wings in place, or alternatively the moulded overcap could be designed to fit snugly over the hinge point of the wings, and the wings held in place by a soluble tape, such that when the soluble tape releases, the overcap would be discharged from the capsule by the motion of the wings as they move out to the extended position shown in FIG. 16.

Figure 16:
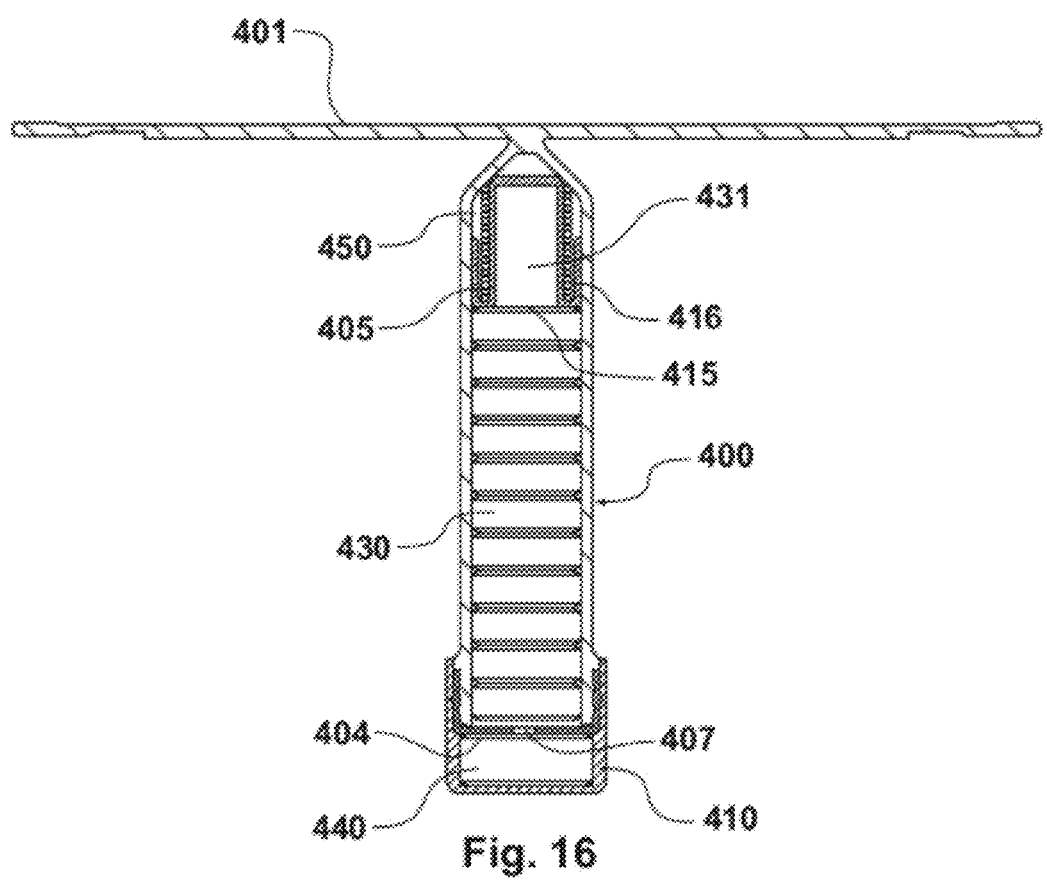

Although such a modified overcap and its dump dose payload would be able to be released into the rumen shortly after the insertion of the capsule into the animal, this arrangement is less advantageous, in that the overcap no longer covers the aperture leading to the sustained release payload. This means that the sustained release payload may start to be released possibly before the overcap is released from the capsule. Thus it will be appreciated that having the overcap 410 on the end of the capsule as shown in FIGS. 15 and 16 distant from the anchor point of the wings 401, there is a clear distinction between release of the dump dose of medicament before the commencement of the release of the sustained release dose of medicament, and before the release of the exit dose of medicament. However there may be some cases where the provision of a dump dose at the wing end of the capsule may be advantageous, and there may be some cases where it is desirable to have a dump dose at both ends of the capsule, one at the anchor point of the wings and one at the other end of the capsule distant from the anchor point of the wings.

Many other variations are possible.

Exit Dose

It is also desirable for a sustained release capsule to include an exit dose that can be released at the conclusion of the sustained release payout period instead of, or as well as, the dump dose. If the capsule is used to release a medicament such as an anthelmintic over a long period, the exit dose would preferably be in the form of a larger immediate release of anthelmintic sufficient to kill any parasites that may have survived the low level of sustained release of anthelmintic. However there are practical problems with achieving this desired embodiment.

Just as there are difficulties in providing for a priming dose within the body of the capsule the same basic problems are present when including an exit dose. Because the fast release exit tablet must be constructed of a more soluble formulation than the sustained release tablets this can result in the release of the anthelmintic drug through the matrix of the sustained release medicament or tablet stack before it is meant to be released. There is also an additional problem of how to fit such an exit dose into the device when it is desired to include as much medicament or as many sustained release tablets into the capsule as possible.

To address these issues, the next embodiment of the invention allows for the inclusion of an exit dose of medicament in a modified piston covering the end of the spring within the capsule device. Current sustained release capsules fitted with a spring have a flat faced piston (which serves as the spring cover). This cover contacts the face of the last sustained release tablet within the tablet stack inside the capsule. There is however a void space within the inner diameter of the spring behind the spring cover. This space is currently not utilised for any practical purpose.

Example 3

FIGS. 8-14 of the attached drawings provide an example of a third embodiment of the invention, which is capable of providing an exit dose of material to the rumen of a ruminant animal.

The capsule 300 is shown in side elevation in FIG. 9. The capsule 300 has a pair of foldable wings 301, and an apertured 307 end face 304, generally of the type as described in examples 1 and 2. FIG. 8 shows a rib 306 on the underside of the wings 301.

Inside the capsule device 300 there is a modified moveable piston, indicated generally at 305 of FIG. 9. This piston is modified in the sense that it no longer has a sealed end face, but has an aperture 315 at the centre of the end face 320 which leads into a hollow chamber 316 in which an exit dose of medicament can be stored. This hollow chamber 316 forms the central sleeve 317 about which a coil spring (not shown until FIGS. 15 and 16) can be positioned and held in the outer sleeve 318 and compressed between end face 320 and stop 322, so that the coil spring biases the medicament or tablet stack contained within the body of the device (as shown at 330 in FIG. 13) towards the exit end 304 of the device. The exit end face 304 is securely held in place by a screw thread 308 or the like as previously described, and has a central aperture 307 which aligns with the central aperture 315 in the end face 320 of the moveable piston.

The moveable piston 305 is shown in more detail in FIGS. 10 (in side elevation), 11 (in end elevation) and 12 (in cross section).

FIG. 13 shows an embodiment of the capsule containing a stack of tablets 330 in the main body of the capsule. The moveable piston 305 is located at the end of the capsule device where the wings are attached, and as the tablets are sequentially dissolved by the rumen fluid entering through the aperture 307 in the end face 304, the dissolved material is gradually forced out of the aperture in the end face by the moveable piston 305 moving under the influence of the spring towards the end face 304.

When the moveable piston 305 reaches the end face 304 as shown in FIG. 14, it will be apparent that the aperture 307 in the end face is aligned with the aperture 315 in the central chamber 316 of the moveable piston, and any material stored in chamber 316 as an exit dose, will then be released into the rumen. FIG. 13 shows an exit dose of medicament 331 contained within the chamber 316.

Typically the exit dose 331 will be a fast release tablet, which dissolves more quickly than the sustained release formulations of the payload 330 in the body of the capsule, and hence the material of the exit dose will be released quickly into the rumen.

Because the exit dose 331 is stored within a chamber 316 in the modified piston, it does not add to the length of the capsule, and this exit dose configuration can also work with the dump dose configuration of examples 1 and 2.

Example 4

FIGS. 15 and 16 show a capsule generally indicated at 400 which combines the features of Examples 1 and 3, namely an external biodegradable overcap 410 containing an initial dump dose of medicament 440, and a modified piston 405 inside the capsule containing an exit dose of medicament 431.

Both FIGS. 15 and 16 are sectional views (similar to the sectional view of FIG. 2 based on a similar section A-A) except that FIG. 15 shows the wings 401 folded prior to insertion of the capsule into an animal. When fully assembled with the wings 401 folded downwards as in FIG. 15, the wings can be held in place by a biodegradable attachment such as a tape made from starch or other dissolvable material. FIG. 15 shows that the wings when folded do not touch the moulded overcap but that the wings themselves are of a thickness comparable to the wall thickness of the overcap so that the wings and moulded overcap provide a relatively smooth exterior to the capsule to enable it to be swallowed by the animal.

FIG. 15 shows the moulded overcap 410, preferably moulded from a biodegradable starch material, sitting over the end closure 404 of the capsule, the end closure 404 having a central aperture 407 to allow the subsequent release of the medicament inside the capsule after the overcap has been detached from the capsule body. Inside the capsule body there is a sequence of tablets 430 preferably containing a sustained release composition or compositions so that the payload inside the capsule can be released slowly over time as the rumen fluid enters through the aperture 407 and successively dissolves the material of each tablet. Although it is preferred to use tablets, other dosage forms can be used inside the body of the capsule. The tablet stack 430 shown in FIG. 15 is biased towards the exit aperture 407 by means of a coil spring 450 shown fitted within the recess of the piston 405. As described in Example 3, this piston has a central chamber 416 having an aperture 415 opening towards the tablet stack, which enables an exit dose of medicament to be positioned in this chamber. This chamber 416 and its aperture 415 will eventually be able to access the aperture 407 in the end closure 404 when all of the tablets have been dissolved and the coil spring 450 has pushed the piston 405 towards the end closure 404 of the capsule.

FIG. 16 shows the capsule containing a dump dose of medicament 440, a sustained release tablet stack 430, and an exit dose of medicament 431, but with the wings 401 extended, as they would be shortly after insertion of the capsule into the rumen, and before the moulded overcap 410 had been dissolved enough to be released from the end of the capsule body.

Dimensions:

The device of FIGS. 15 and 16 shows the device printed on a scale of 1:1. However the device can be made in many different sizes depending on the size of the animal for which it is intended.

FIG. 15 shows a suitable sized device for cattle weighing from 100 to 200 kg. The precise size and dimensions of the same sustained release capsule depend upon the size of the animal into which it is being inserted. For example, the device may be produced in five different sizes, a small unit for a weaner lamb, a slightly larger version for adult sheep, an intermediate version as shown in FIG. 15 for weaner cattle from 100 to 200 kg in size, a larger size for larger weaner cattle weighing from 200 to 300 kg, and a larger size for adult cattle weighing from 400 to 600 kg.

Of course many other variations are possible, and the size and in particular the length of the device may depend upon the payload and the design time of the payout of the payload.

Advantages of the Exit Dose Configuration (Example 3 and the Combined Configuration of Example 4)

By designing the piston to include a well shaped portion projecting rearward from the face that contacts the last sustained release tablet, a suitable repository can be created to contain an exit dose of medicament.

The well shaped portion has an additional advantage to merely creating a suitable repository for the exit dose material. That is, it also concentrates the exit dose material at the centre of the tablet stack where it is aligned with the aperture 407 once the capsule has paid out the sustained release tablet stack portion 430. Because each tablet in the sustained release tablet stack 430 tends to collapse and gellify from the centre portion immediately adjacent the aperture 407 first, this makes it highly desirable that the exit dose medicament is also aligned with this point. This means that even if the last sustained release tablet is not completely paid out the exit dose 431 will still be cleanly and effectively released.

Because the modified piston 405 does not impede significantly on the interior volume of the capsule, it is still possible to provide a significant sustained release payload 430 within the body of the capsule and also provide for the provision of an exit dose 431 within the piston 405. Thus the combined capsule of FIGS. 15 and 16, or other variations of this combination concept, will not be unduly long in length, and yet will still provide for the three different types of payload, that is, the dump dose of medicament, the sustained release dose of medicament, and the exit dose of medicament, all within the confines of such a capsule and overcap.

Variation of the Exit Dose Configuration

Instead of a coil spring, any other resilient means can be used to cause the piston to move towards the exit end of the device.

The modified piston of example 3 can be included in the configurations of examples 1 or 2 so that the device has a dump dose and an exit dose as well as the sustained release payload within the body of the capsule, generally as described in Example 4.

Although it is preferable that the dump dose, the sustained release payload, and the exit dose are formulated differently, it is also possible that this configuration could be used to deliver a longer duration sustained release payload by including a sustained release portion in the dump dose, the main payload itself within the capsule, and also in the cavity within the piston, or some sub-combination of these three possibilities.

Although the four embodiments are described with reference to foldable wings, other forms of protrusions or means for retaining the capsule within the rumen can be used.

Field Study

In order to test the efficacy of the invention a field study was performed in respect of an embodiment of the invention comprising a plasticised starch overcap fitted to a sustained release capsule for sheep, the overcap comprising a dump dose of medicament. This was a single dose, controlled total worm count efficacy study in which the dump dose medicament contained within the overcap on the capsule comprised a combination of abamectin and levamisole, while the sustained release medicament contained within the body of the capsule comprised a combination of abamectin and albendazole designed to be released over a period of 100 days.

An untreated control group, a group treated with an empty capsule fitted with the overcap comprising the dump dose only, and a group treated with a standard abamectin/albendazole sustained release capsule were also included in the study.

Four days prior to treatment, a group of 30 sheep suspected of harbouring a burden of gastrointestinal parasites and weighing between 60 kg-80 kg were selected from a larger mob, ear tagged and faecal sampled for faecal egg count (FEC). From this mob of sheep, 24 animals with positive FEC were selected for inclusion in the study. Animals were introduced to a diet of lucerne chaffage whilst on pasture.

On Day 0 the study animals were removed from pasture, weighed and randomly assigned to 4 groups of n=6 based on individual bodyweight. All animals were faecal sampled for FEC and larval culture and the treatments were administered to animals in Groups 1-3; while Group 4 remained untreated. Animals were retained off pasture for the duration of the study. Treatment groups were:

Group 1: Abamectin/albendazole sustained release capsule including an overcap comprising a dump dose of medicament containing abamectin and levamisole Group 2: Empty sustained release capsule with an overcap comprising a dump dose of medicament containing abamectin and levamisole Group 3: Abamectin/albendazole sustained release capsule with no dump dose overcap Group 4: Untreated control Ten days after treatment, all study animals were faecal sampled for FEC to demonstrate faecal egg count reduction and confirm control group worm burdens. A larval culture was performed on pooled faeces from Group 4. The following day, all animals were necropsied and the abomasa, small and large intestines were collected for total worm counts. Individual capsules were recovered from treated animals in Groups 1 and 3 and measured to determine release kinetics. Capsules fitted with the overcap containing the dump dose of medicament (Groups 1 and 2) were examined to ensure the housing and tablet had detached correctly.

Results

Performance of the Overcap Containing the Dump Dose of Medicament

Performance of the overcap containing the dump dose of medicament was measured by the ability of the actives in the overcap (abamectin/levamisole) to reduce worm burdens in the animals. This was principally demonstrated by comparing the result from Group 2 with the other treatment Groups.

Total Worm Counts:

Mean total worm count results are shown in Tables 1a, 1b and 1c. The control group harboured a mixed burden of gastrointestinal nematodes, evident from the total worm count results.

TABLE 1a

Arithmetic and geometric mean total worm counts - Abomasum

| | Species | | | | | |
|---|---|---|---|---|---|---|
| | Haemonchus contortus | | Ostertagia/ Teladorsagia spp. | | Trichostrongylus axei | |
| Stage | Adult | Immature | Adult | Immature | Adult | Immature |
| | Arithmetic means | | | | | |
| Group 1 | 0.0 | 0.0 | 0.0 | 0.0 | 0.0 | 0.0 |
| Group 2 | 0.0 | 0.0 | 16.7 | 0.0 | 0.0 | 0.0 |
| Group 3 | 0.0 | 0.0 | 0.0 | 0.0 | 0.0 | 0.0 |
| Group 4 | 50.0 | 8.3 | 1108.3 | 16.7 | 3850.0 | 0.0 |
| | Geometric means | | | | | |
| Group 1 | 0.0 [a] | 0.0 [a] | 0.0 [a] | 0.0 [a] | 0.0 [a] | 0.0 [a] |
| Group 2 | 0.0 [a] | 0.0 [a] | 2.7 [a] | 0.0 [a] | 0.0 [a] | 0.0 [a] |
| Group 3 | 0.0 [a] | 0.0 [a] | 0.0 [a] | 0.0 [a] | 0.0 [a] | 0.0 [a] |
| Group 4 | 8.6 [b] | 0.9 [a] | 614.2 [b] | 1.2 [a] | 2943.6 [b] | 0.0 [a] |

[a, b] Subscripts within the same column are not significantly different at $p < 0.05$

TABLE 1b

Arithmetic and geometric mean total worm counts - Small intestine

| | Species | | | | | |
|---|---|---|---|---|---|---|
| | Nematodirus spp. | | Trichostrongylus spp. | | Cooperia spp. | |
| Stage | Adult | Immature | Adult | Immature | Adult | Immature |
| | Arithmetic means | | | | | |
| Group 1 | 0.0 | 0.0 | 0.0 | 0.0 | 0.0 | 0.0 |
| Group 2 | 0.0 | 0.0 | 0.0 | 0.0 | 0.0 | 0.0 |
| Group 3 | 0.0 | 0.0 | 0.0 | 0.0 | 0.0 | 0.0 |
| Group 4 | 366.7 | 100.0 | 1750.0 | 8.3 | 508.6 | 0.0 |
| | Geometric means | | | | | |
| Group 1 | 0.0 [a] | 0.0 [a] | 0.0 [a] | 0.0 [a] | 0.0 [a] | 0.0 [a] |
| Group 2 | 0.0 [a] | 0.0 [a] | 0.0 [a] | 0.0 [a] | 0.0 [a] | 0.0 [a] |
| Group 3 | 0.0 [a] | 0.0 [a] | 0.0 [a] | 0.0 [a] | 0.0 [a] | 0.0 [a] |
| Group 4 | 93.1 [b] | 49.1 [b] | 1582.2 [b] | 0.9 [a] | 22.3 [b] | 0.0 [a] |

[a, b] Subscripts within the same column are not significantly different at $p < 0.05$

TABLE 1c

Arithmetic and geometric mean total worm counts - Large intestine

| | Species | | |
|---|---|---|---|
| | Oesophagostomum spp. | Chabertia spp. | Trichuris spp. |
| Stage | Adult | Adult | Adult |
| | Arithmetic means | | |
| Group 1 | 0.0 | 0.0 | 0.0 |
| Group 2 | 0.0 | 0.0 | 0.0 |
| Group 3 | 0.0 | 0.0 | 0.0 |
| Group 4 | 43.3 | 6.7 | 23.3 |
| | Geometric means | | |
| Group 1 | 0.0 [a] | 0.0 [a] | 0.0 [a] |
| Group 2 | 0.0 [a] | 0.0 [a] | 0.0 [a] |
| Group 3 | 0.0 [a] | 0.0 [a] | 0.0 [a] |
| Group 4 | 31.1 [b] | 2.7 [b] | 20.5 [b] |

[a, b] Subscripts within the same column are not significantly different at $p < 0.05$ Percent Efficacy (% E) for each group was calculated for each of the worm species (WS) present, using the following formula:

$$\% E = \frac{\text{Mean of } (WS) \text{ in controls} - \text{mean of } (WS) \text{ in treated group}}{\text{Mean of } (WS) \text{ in controls}} \times 100$$

Percentage efficacies calculated on total worm counts using both arithmetic and geometric means are shown in Table 2a, 2b and 2c.

TABLE 2a

Percentage efficacies (by genus, based on abomasa Total Worm Counts)

| | Haemonchus contortus | Ostertagia/Teladorsagia spp | Trichostrongylus axei |
|---|---|---|---|
| | % Arithmetic Efficacy | | |
| Group 1 | 100 | 100 | 100 |
| Group 2 | 100 | 98.5 | 100 |
| Group 3 | 100 | 100 | 100 |

TABLE 2a-continued

Percentage efficacies (by genus, based on abomasa Total Worm Counts)

| | Haemonchus contortus | Ostertagia/Teladorsagia spp | Trichostrongylus axei |
|---|---|---|---|
| % Geometric Efficacy | | | |
| Group 1 | 100 | 100 | 100 |
| Group 2 | 100 | 99.6 | 100 |
| Group 3 | 100 | 100 | 100 |

TABLE 2b

Percentage efficacies (by genus, based on small intestinal Total Worm Counts)

| | Nematodirus spp. Adult | Nematodirus spp. Immature | Trichostrongylus spp. | Cooperia spp. |
|---|---|---|---|---|
| % Arithmetic Efficacy | | | | |
| Group 1 | 100 | 100 | 100 | 100 |
| Group 2 | 100 | 100 | 100 | 100 |
| Group 3 | 100 | 100 | 100 | 100 |
| % Geometric Efficacy | | | | |
| Group 1 | 100 | 100 | 100 | 100 |
| Group 2 | 100 | 100 | 100 | 100 |
| Group 3 | 100 | 100 | 100 | 100 |

TABLE 2c

Percentage efficacies (by genus, based on large intestinal Total Worm Counts)

| | Oesophagostomum spp. | Chabertia spp. | Trichuris spp. |
|---|---|---|---|
| % Arithmetic Efficacy | | | |
| Group 1 | 100 | 100 | 100 |
| Group 2 | 100 | 100 | 100 |
| Group 3 | | 100 | 100 |
| % Geometric Efficacy | | | |
| Group 1 | 100 | 100 | 100 |
| Group 2 | 100 | 100 | 100 |
| Group 3 | 100 | 100 | 100 |

Performance of the Sustained Release Medicament within Capsule Body

To ensure that the overcap comprising the dump dose of medicament had no effect on the payout of the sustained release portion of the device, the linear payout of the tablet stack within the device having the dump dose overcap fitted (Group 1) was compared with the linear payout of that from a standard device having no dump dose portion fitted (Group 3). The result was that the mean linear payout for Groups 1 and 3 was 7.85 and 7.91 mm respectively, eleven days after administration. It can therefore be concluded that the overcap quickly detached from the sustained release capsule and that the addition of the dump dose cap element to the sustained release device had no effect on the subsequent linear payout when compared to the standard device, p=0.87.

The invention claimed is:

1. A sustained release capsule comprising:
   a) a hollow tubular body sealed at a first end,
   b) a movable piston within the body,
   c) a spring biasing the piston towards a second end of the body,
   d) an apertured cover at the second end to define a first chamber between the movable piston and the apertured cover capable of containing a first dose of material within the hollow tubular body for subsequent sustained release through the apertured cover into a rumen of an animal, and
   wherein the movable piston has an end face facing towards the first dose, a hollow central sleeve extending rearwardly from the end face to assist in locating a spring, an aperture in the end face into a hollow interior of the central sleeve, the central sleeve having a closed portion distal from the end face to create a void capable of containing an exit dose of material.

2. The capsule of claim 1 further comprising an overcap which is releasably attached to the second end to form a void between the apertured cover and the overcap capable of containing a second dose of material within the void so that in use the second dose of material is delivered to the rumen when the overcap is breached or detaches from the second end.

3. The capsule of claim 2 wherein the overcap is releasably attached to the device by a dissolvable attachment.

4. The capsule of claim 2 wherein the overcap is made of a material which will dissolve or breakup in the rumen.

5. The capsule of claim 2 wherein the overcap is made of a material selected from the group consisting of cellulosic fibre, cardboard, paper, a water soluble plastics material and starch.

6. The capsule of claim 2 wherein the capsule is loaded with a second dose of material in the overcap.

7. The capsule of claim 6, wherein the second dose of material in the overcap comprises copper needles.

8. The capsule of claim 1 wherein the body has at least one external protrusion adapted in use to assist in retaining the capsule in the rumen of an animal.

9. The capsule of claim 8 wherein the at least one protrusion consists of a pair of foldable wings.

10. The capsule of claim 1 wherein the capsule is loaded with a first dose of material.

11. The capsule of claim 1 wherein the capsule is loaded with an exit dose of material.

* * * * *